United States Patent
Fox et al.

(10) Patent No.: US 9,998,511 B2
(45) Date of Patent: *Jun. 12, 2018

(54) SCALABLE EVENT STREAM DATA PROCESSING USING A MESSAGING SYSTEM

(71) Applicant: International Business Machines Corporation, Armonk, NY (US)

(72) Inventors: Timothy M. Fox, Lakewood, OH (US); Anyi Li, Rocky River, OH (US); Scott J. McCallen, Stow, OH (US); Douglas S. Meil, Chagrin Falls, OH (US); Kaveh Noorbakhsh, Mayfield Heights, OH (US)

(73) Assignee: International Business Machines Corporation, Armonk, NY (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/635,774

(22) Filed: Jun. 28, 2017

(65) Prior Publication Data

US 2017/0302710 A1    Oct. 19, 2017

Related U.S. Application Data

(63) Continuation of application No. 14/993,160, filed on Jan. 12, 2016.

(51) Int. Cl.
*G06F 15/16* (2006.01)
*H04L 29/06* (2006.01)
(Continued)

(52) U.S. Cl.
CPC .... *H04L 65/4076* (2013.01); *G06F 17/30312* (2013.01); *G06F 17/30516* (2013.01); *G06F 19/322* (2013.01)

(58) Field of Classification Search
USPC ....... 709/203, 206, 207, 217, 219, 223, 224, 709/226, 228, 231, 232, 238; 700/96;
(Continued)

(56) References Cited

U.S. PATENT DOCUMENTS

2003/0158615 A1* 8/2003 Weber .................... B65G 37/02
700/96
2006/0265455 A1* 11/2006 Yakushev ............... G06F 9/546
709/206

(Continued)

OTHER PUBLICATIONS

Sharma, Apache Kafka: Next Generation Distributed Messaging System, http://www.infoq.com/articles/apache-kafka, Jun. 4, 2014, 18 pages.

(Continued)

*Primary Examiner* — Quang N Nguyen
(74) *Attorney, Agent, or Firm* — Ingrid M. Foerster; SVL IP Law Edell, Shapiro & Finnan, LLC

(57) ABSTRACT

A system processes streaming data and includes at least one processor. The system may write streaming data received from a data source as messages in queues at a queuing cluster. The queuing cluster includes a coordinator node to direct the messages to non-coordinator nodes of the queuing cluster. The system may retrieve the data from the queues based on subscription of topics and store the retrieved data in a consumable repository.

7 Claims, 7 Drawing Sheets

(51) Int. Cl.
*G06F 17/30* (2006.01)
*G06F 19/00* (2018.01)

(58) Field of Classification Search
USPC .......................................................... 370/390
See application file for complete search history.

(56) References Cited

U.S. PATENT DOCUMENTS

| | | | |
|---|---|---|---|
| 2014/0032240 A1 | 1/2014 | Lougheed et al. | |
| 2014/0105208 A1* | 4/2014 | Pope | G06F 13/385 370/390 |
| 2016/0344605 A1* | 11/2016 | Branson | G06F 11/3636 |
| 2016/0364218 A1* | 12/2016 | Barsness | G06F 8/43 |
| 2016/0371171 A1* | 12/2016 | Barsness | G06F 11/362 |
| 2017/0153966 A1* | 6/2017 | Cao | G06F 11/3664 |

OTHER PUBLICATIONS

Apache Kafka Overview, http://www.cloudera.com/content/www/en-us/documentation/kafka/1-2-x/ . . . , Cloudera Distribution of Kafka 1.2.x, 2015 Cloudera, Inc., 1 page.
Apache Kafka, Kafka 0.9.0 Documentation, http://kafka.apache.org/documentation.html#introduction, retrieved from internet Dec. 15, 2015, 90 pages.
Nabi et al., Of Streams and Storms, Apr. 2014, 31 pages.
Stein, Apache Kafka Real-Time Data Pipelines, http://kafka.apache.org/, Apr. 9, 2014, 40 pages.
List of IBM Patents or Patent Applications Treated as Related, Jun. 2017, 1 page.
"The Explorys Platform", IBM Watson Health, Solution Brief, Produced in the United States of America, Nov. 2015, 4 pages.

* cited by examiner

SCALABLE EVENT STREAM DATA PROCESSING USING A MESSAGING SYSTEM

CROSS-REFERENCE TO RELATED APPLICATIONS

This application is a continuation of U.S. patent application Ser. No. 14/993,160, entitled "SCALABLE EVENT STREAM DATA PROCESSING USING A MESSAGING SYSTEM" and filed Jan. 12, 2016, the disclosure of which is incorporated herein by reference in its entirety.

BACKGROUND

1. Technical Field

Present invention embodiments relate to integration of data for a computing system from a plurality of data sources, and more specifically, to event stream processing of data using message queuing.

2. Discussion of the Related Art

A healthcare network typically comprises multiple source systems (e.g., a source of electronic medical records including electronic healthcare records (EHR), records from a claims system, lab feed, various data sources implementing the Health Level Seven (HL7) standard, patient satisfaction survey, etc.) and applies analytics to various electronic medical records (e.g., EHR, claims system, lab feed, HL7, patient satisfaction survey, etc.) to produce results for a desired population (e.g., patients, healthcare providers, insurance providers, provider organizations or networks, etc.). Communication between different components or systems in a healthcare network is typically implemented as an event driven processing system. Conventional event streaming systems primarily focus on single-server extract, transform and load (ETL) processing. Scalability is very limited for the conventional event streaming systems. In some cases, these systems can be scaled using traditional scaling techniques, such as load balancers and manually configured routing, to balance the transmission of stream data between nodes in the system. They also employ traditional resilience and replication patterns to the stream processing, including high availability proxy, persisting stored data to files and RDBMSs, and replicating between nodes based on manual configurations. The traditional techniques, however, cannot sufficiently satisfy the needs for a modern healthcare network.

SUMMARY

According to one embodiment of the present invention, a system processes streaming data and includes at least one processor. The system may write streaming data received from a data source as messages in queues at a queuing cluster. The queuing cluster includes a coordinator node to direct the messages to non-coordinator nodes of the queuing cluster. The system may retrieve the data from the queues based on subscription of topics and store the retrieved data in a consumable repository. Embodiments of the present invention further include a method and computer program product for processing streaming data.

According to a further embodiment, the system may further listen for the streaming data to be available in the queues by a processing node. The streaming data may be event data for one or more events at the data source. The system may read each event from the queues by the processing node and transform the events to a data model of the consumable repository. In a further embodiment, the system may further manage the processing node by a coordinator node of a processing cluster and retry processing of the streaming data on a different processing node until successful in response to the processing node encountering a failure.

According to yet another further embodiment, the streaming data includes patient data received from a healthcare network. According to an additional embodiment, the consumable repository is a queuing system including a coordinator node to direct the processing node to write the retrieved data to a non-coordinator node in the consumable repository. Additionally, the queuing cluster and consumable repository each may include multiple non-coordinator nodes that provide automated replication and failover through management by the respective coordinator nodes.

In yet another further embodiment, the system may perform one or more operations from a group of routing the retrieved data to different long term storage and pushing the retrieved data to a number of different services that satisfy specific business needs. Moreover, in an additional embodiment, the system may concurrently retrieve data from the consumable repository by a plurality of consumers, wherein the consumers maintain respective pointers to track data that each consumer has processed.

BRIEF DESCRIPTION OF THE DRAWINGS

Generally, like reference numerals in the various figures are utilized to designate like components.

DETAILED DESCRIPTION

An exemplary embodiment healthcare network may implement an event driven processing system that has low latency, horizontally scalable healthcare event stream processing. The event driven processing system may consume remote event streams, transmit the stream to a central message queuing and processing cluster that performs filtering, data enhancement, transformation and finally load the results to a consumable repository. Input event/stream data may be according to specifications in the Health Level 7 standards, such as HL7 v2.x and v3, x12 standard 837 documents, Internet Of Things (IoT) streaming interfaces, and telemetry data. Low latency, in this context interchangeable with Near Real-Time (NRT), may provide meaningful record-by-record ETL and aggregations in a timeframe small enough to provide meaningful and actionable insights to consumers, such as healthcare practitioners (care givers, care coordinators, nurses, doctors, etc.).

Present invention embodiments may process healthcare data like 837 and HL7 messages using a horizontally scalable messaging system that has advantages over processing them with other messaging queues. Horizontally scalable in this case means that the processing of incoming messages can be distributed over an easily scalable distributed computing system or grid. The advantage of being horizontally scalable is that it allows for fast processing of massive quantities of messages, and if the system begins to be overwhelmed, the addition of more nodes to scale is a fast solution. Being able to scale in this fashion will be increasingly important as industry pushes to be closer and closer to real time. The use of a horizontally scalable messaging system also allows the logic for processing 837 and HL7 messages to be built directly into the message consumer. Furthermore, the consumers can write directly to the node they are run on, making the processed message immediately available for ingestion into distributed computing processes (i.e. Map Reduce). Current industry solutions are not able to distribute processing of messages as effectively (messages must flow through a predetermined channel or endpoint), scale as easily, or output messages locally for ingestion into distributed computing algorithms.

Figure 1:
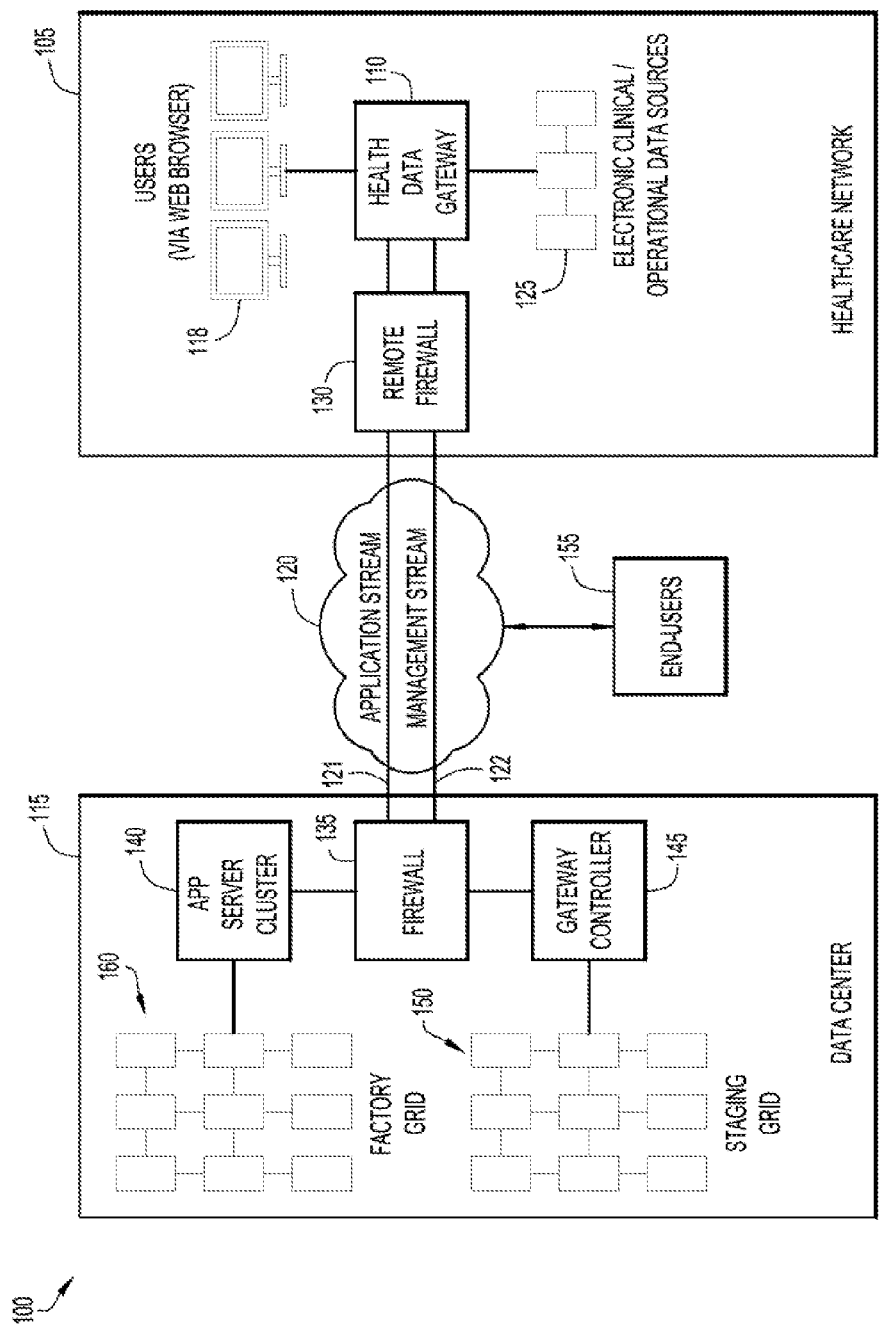
FIG. 1 is a diagrammatic illustration of an example computing environment according to an embodiment of the present invention.

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
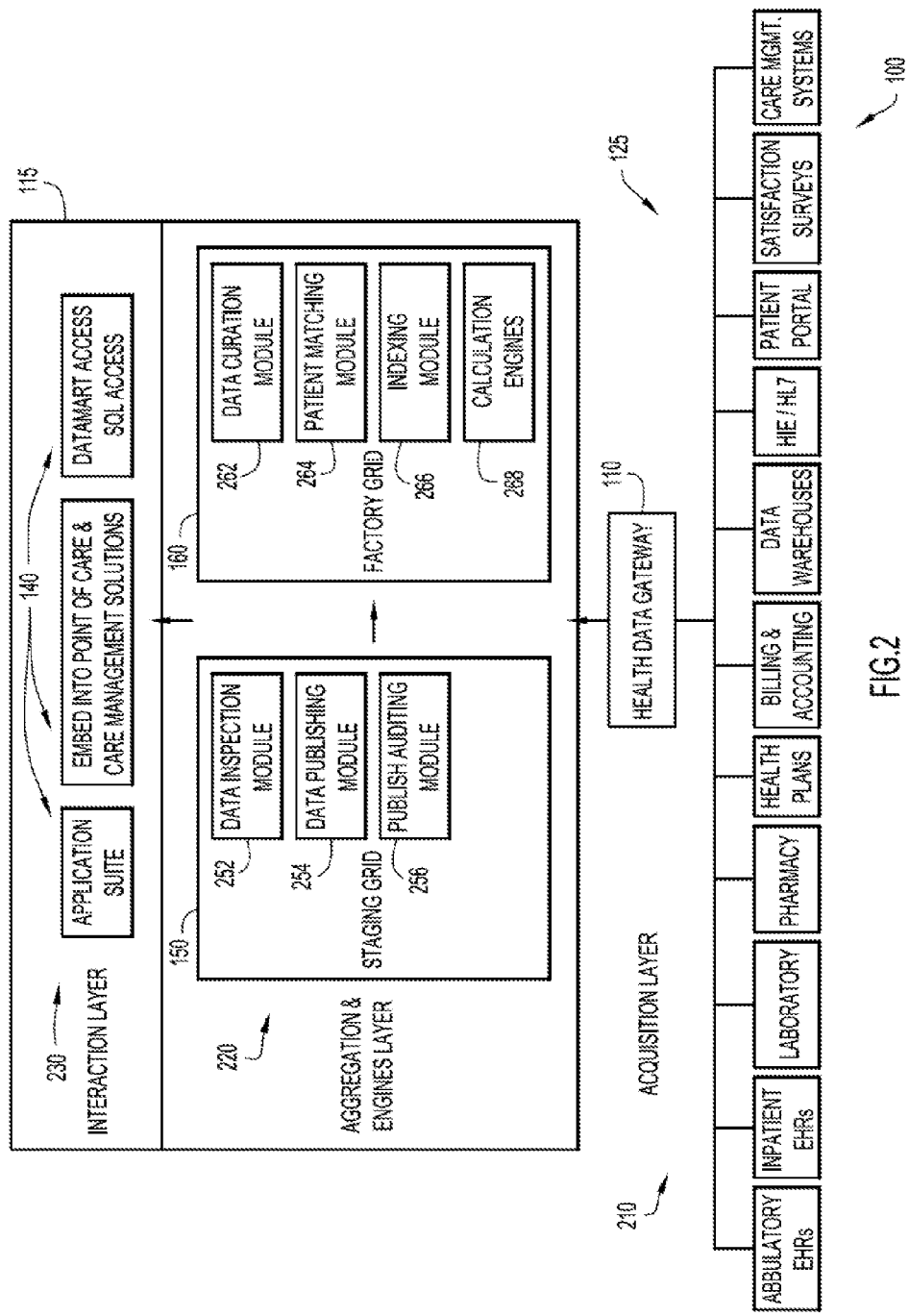
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, and various calculation/analytic engines 268. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines perform the desired analytics based on queries received from end-users from an interaction layer 230 enabling application server cluster 140 to provide various applications for processing and accessing the data (e.g., analytic applications, SQL access, etc.). The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
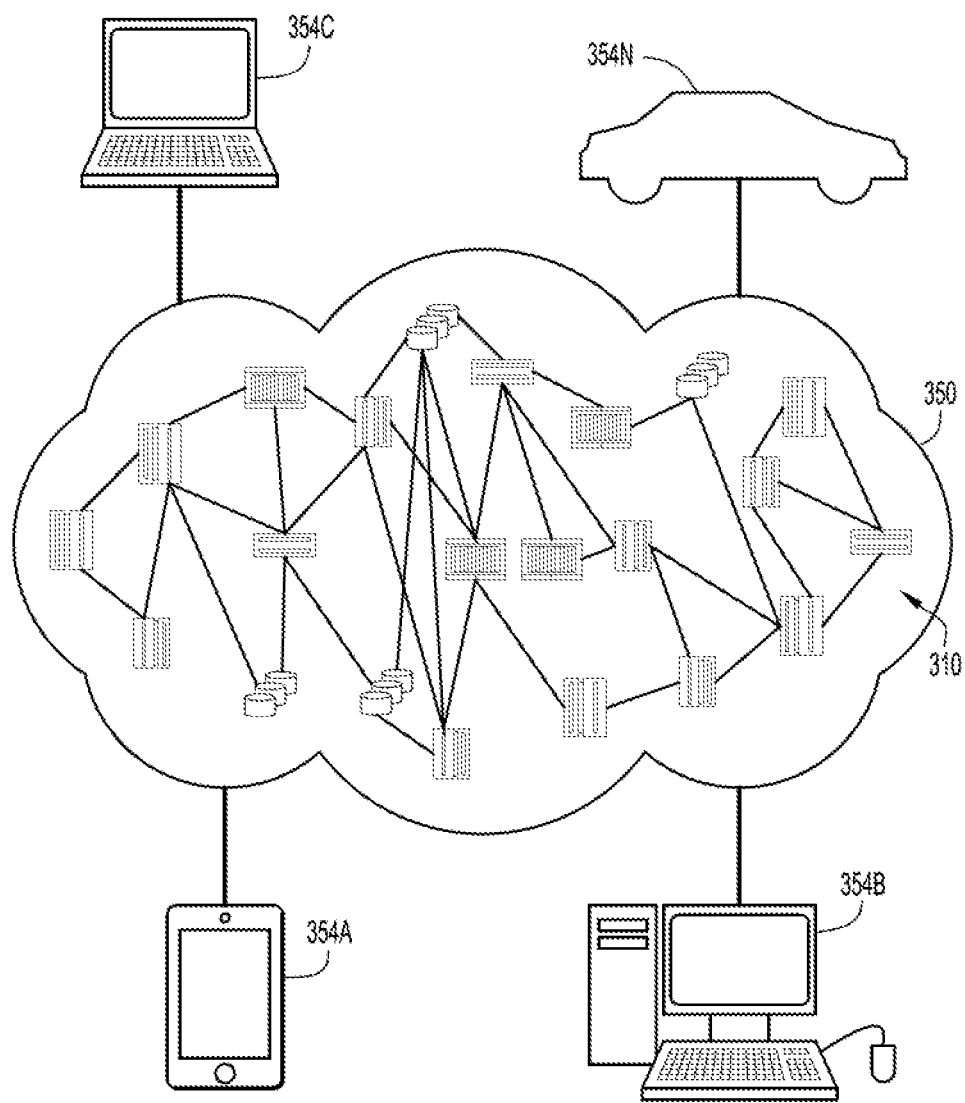
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
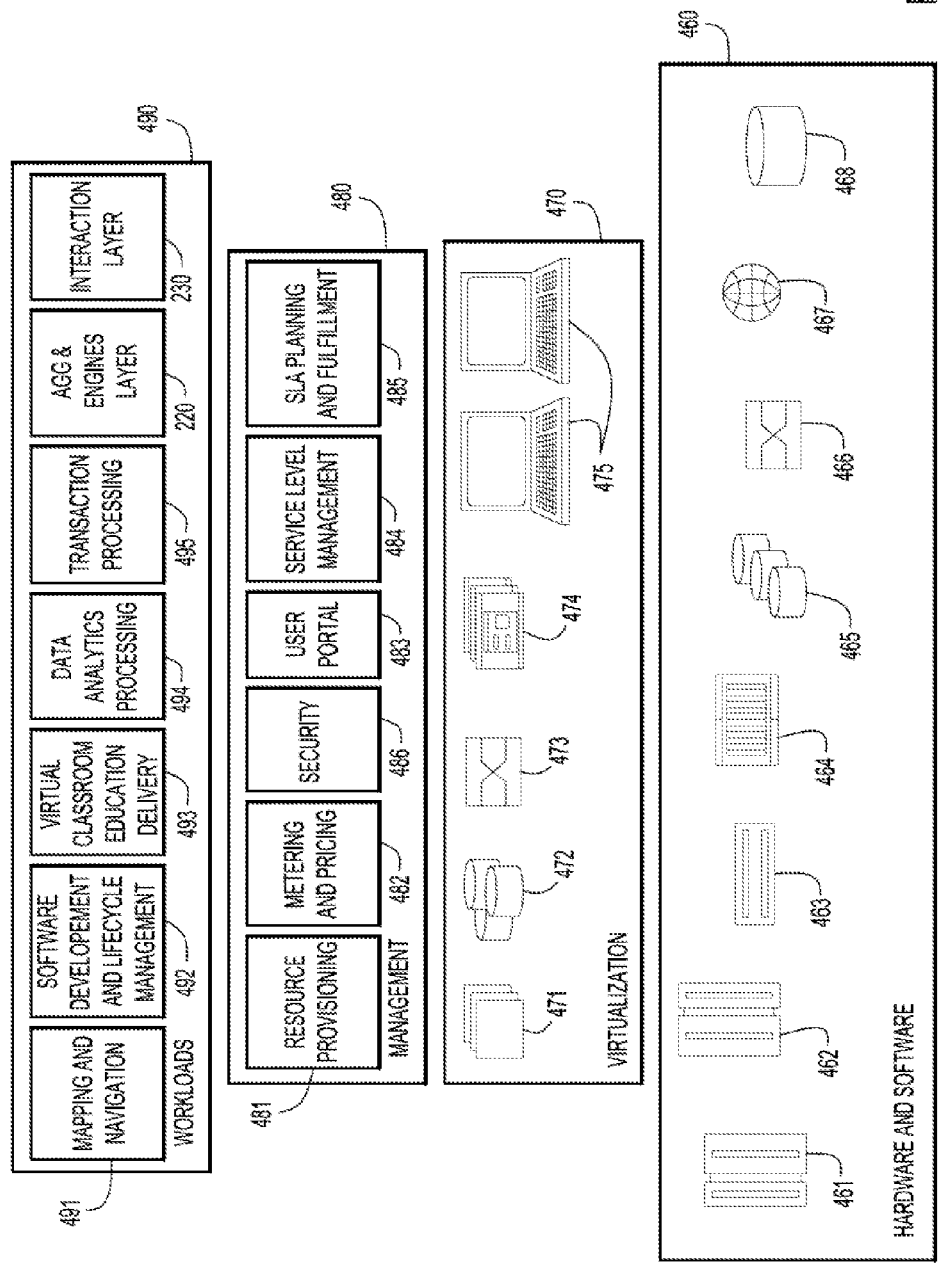
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
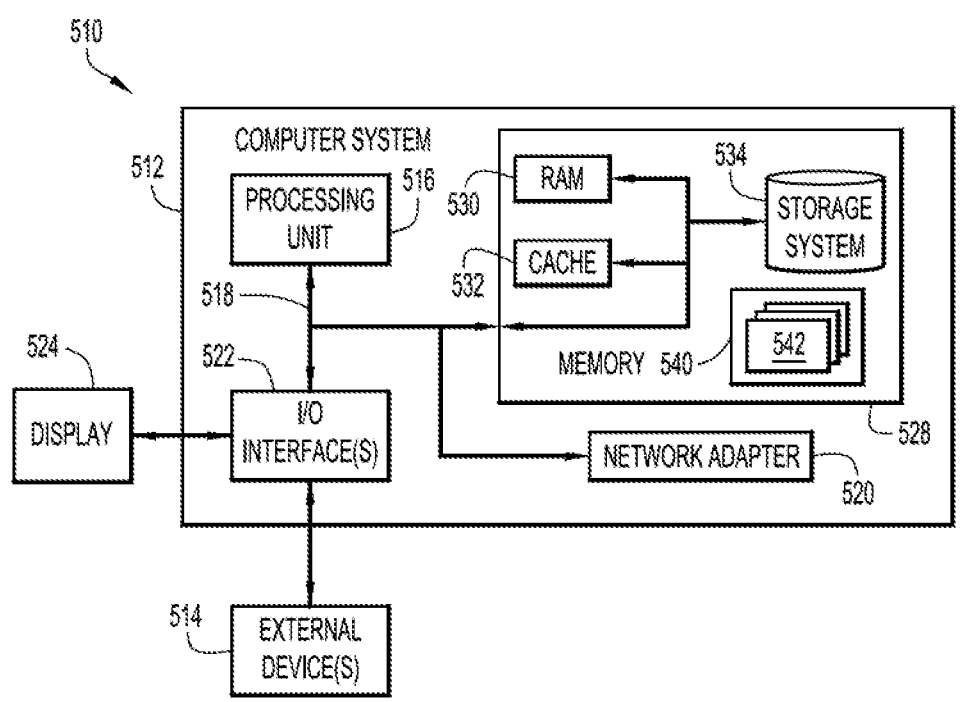
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6:
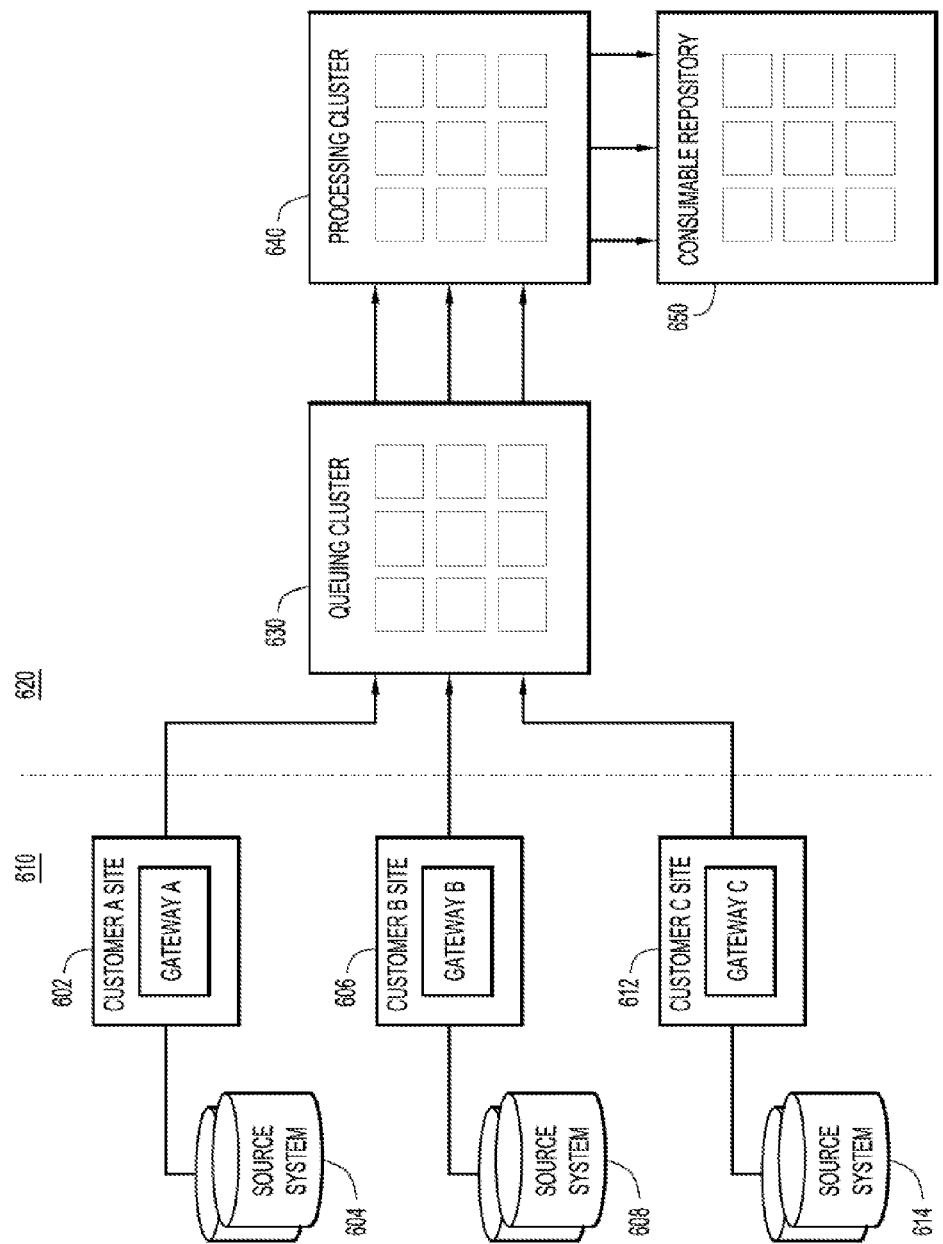
FIG. 6 is a flow diagram of processing healthcare data from different data sources at a data center according to an embodiment of the present invention.

FIG. 6 shows flow of data in an example healthcare network that comprises multiple data sources 610 and a data center 620. The data sources 610 may comprise a customer A site 602, a customer B site 606 and a customer C site 612. Each customer site may comprise one or more respective data sources (e.g., data source 604, 608 and 614) and a respective health data gateway (e.g., gateway A, gateway B and gateway C). For example, the customer A site 602 may comprise one or more data sources 604 and a gateway A, the customer B site 606 may comprise one or more data sources 608 and a gateway B, and the customer C site may comprise one or more data sources 614 and a gateway C. The gateways A, B and C may each be an embodiment of the health data gateway 110 as described herein and may be configured to receive or pull data from event streams, such as HL7 over TCP, 837 documents, relational database management systems (RDBMS), audit logs, continuity of care documents (CCDs), consolidated continuity of care documents (C-CDA), etc. For example, the gateway A may be configured to extract patients, locations and providers data from RDBMS in the data source 602, while the gateway B and gateway C may each be configured to extract data from comma-separated values (CSV) files, 837 files and HL7 over TCP.

Embodiments of the heath data gateways may connect to a stream of events (through some well-known API, such as HL7 over TCP/IP) that may include results of a recurring query to an EHR RDBMS, the events streamed from an RDBMS audit log, or both. These events may be captured by a stream ingestion processor implemented by the gateways and immediately, record by record, forwarded to a central queuing cluster. For example, after extracting the data from the data sources, each of the health data gateways (e.g., the gateways A, B, and C) may stream the received or pulled data to the data center 620 (e.g., the queuing cluster 630).

The data center 620 may be an embodiment of the data center 115 as described herein and may comprise a queuing cluster 630, a processing cluster 640 and a consumable repository 650. In this embodiment, the gateway controller 145 may be optional (e.g., either not exist or play a very minimal role). The queuing cluster 630, processing cluster 640 and consumable repository 650 may be part of the aggregation and engines layer 220 such that the staging grid 150 (and/or factory grid 160) may implement the queuing cluster 630, processing cluster 640 and consumable repository 650. The data center 620 may receive the data sent by the health data gateways (e.g., the gateways A, B, and C) at the queuing cluster 630. The queuing cluster 630 may be implemented by a messaging system that provides very low-latency, resilient message queuing services. In one embodiment, the queuing cluster 630 may include a plurality of computing nodes (e.g., the device 510 of FIG. 5). One or more of the nodes may be coordinator nodes and more than one node may be non-coordinator nodes.

The data streamed by the health data gateways may be received by the queuing cluster 630 as messages and the coordinator nodes of the queuing cluster 630 may write these received messages to a plurality of nodes. In one embodiment, different queues may be created at the queuing cluster 630, for example, according to topics, which may be based on keywords or pre-determined criteria. Each topic may be configured as one individual queue such that messages written to the queue may be logged and stored according a storage structure implemented by the queuing cluster 630. Consumers of the messages may monitor (e.g., listen to) one or more queues based on subscription of the topics.

In one embodiment, messages for one topic may be written to more than one non-coordinator node by the coordinator nodes for load balancing (e.g., in a round robin manner). Moreover, to provide fault tolerance, each non-coordinator node actively receiving and queuing the messages may have one or more duplicate nodes as backup nodes. The active non-coordinator nodes and their backup nodes may be hosted by different physical machines, and the backup nodes may also receive and queue any messages received by the active nodes. Therefore, in case an active non-coordinator node fails, one of its backup nodes can take over without interruption to the messaging service. In some embodiments, the queuing cluster 630 may coordinate with the gateways for transmission of the healthcare data from the gateways and the transmission may be highly redundant.

The queuing cluster 630 may be configured to queue millions of messages per second (or more). Message writes are distributed by coordinator nodes which direct a producer of the message (e.g., the gateways A, B, and C) to write the data to a non-coordinator node in the cluster. Data queuing may be horizontally scalable as needs require, for example, by adding more non-coordinator nodes.

The processing cluster 640 may be a highly available, distributed system that provides processing nodes listening for data to be available in the queuing cluster 630. When data is available in a queue, one or more processing nodes, which may be registered or subscribed consumers for the data, may read each event, record by record, from the queue and perform the configured filtering, data enhancement and transformation to the data model. The resulting record(s) may be written to the consumable repository 650. The processing cluster 640 may also include coordinator nodes and non-coordinator nodes. Coordinator nodes may act as managers to ensure that all data processing is successful and will be retried on different processing non-coordinator nodes until successful, in case of an intermittent failure. The non-coordinator nodes of the processing cluster 640 may be implemented in the staging grid 150 as described herein. In one embodiment, the processing cluster 640 may be implemented as a distributed, resilient processing system that pulls data from the queuing cluster 630 as quickly as possible, transforms the data to a canonical form (e.g., common, well-known, and/or specified by some standard) and pushes the data to the consumable repository 650. The result of the transformation is common record types, such as, but not limited to, Observation, Encounter, Admission, Vital, Procedure, etc.

The consumable repository 650 may provide a landing repository for the records produced by the processing cluster 640, which then become available for downstream consumers. This repository 650 may be implemented as a distributed, resilient file system, or a queuing cluster the same as the queuing cluster 630. The consumable repository 650 may also include coordinator nodes and non-coordinator nodes, and also implement load balancing and fault tolerance similar to the queuing cluster 630. In one embodiment, the consumable repository 650 may contain the transformed data in a common, well-known (canonical) form for consumption by downstream consumers. Data may be queued in the order it is transformed by the processing cluster 640. Each consumer may have a respective pointer pointing to a position in the queued data that represents each consumer's current consumption position in the queued data. Each pointer may be controlled by the respective consumers. That is, a consumer controls its own rate to consume the transformed data without affecting or being affected by the consumption rate of other consumers.

As described above, the central event/message queuing cluster 630, processing cluster 640 and consumable repository 650 have similar attributes. First, they feature coordinator nodes that automate the distribution of storage and processing across the cluster, which provides dynamic horizontal scaling. New storage and/or processing nodes (e.g., non-coordinator nodes) may be added to the cluster and the coordinator nodes may add the new nodes to the pool of available nodes. In this implementation, data may be read or written on the node where the data is stored, as opposed to traditional stream processing where all reads and writes may need to pass through a single head node. Second, they feature automated replication and failover through management by the coordinator nodes that ensure all data writes are persisted to multiple data nodes and all failed processing is retried on another processing node until the processing completes successfully.

The health data gateway and stream ingestion software can be implemented using the health data gateway architecture as shown in FIG. 1 and described herein and the data acquisition software deployed on those machines (e.g., FIGS. 2 and 4 and described herein). Additionally, the stream ingestion could be implemented by open source projects such as, but not limited to, Apache Camel. The queuing cluster 630 and consumable repository 650 may be implemented using a framework such as, but not limited to, Apache Kafka. The processing cluster 640 may be implemented using frameworks such as, but not limited to, Apache Storm, Apache Spark, or IBM Infosphere Streams.

Embodiments having a message cluster as the consumable cluster 650 at the end of the transformation pipeline may provide several benefits. One of such benefits may be decoupling the staging grid (where the transform happens) from the factory grid (where the analytic algorithms are processed). For example, the pipeline (e.g., from the gateways to the queuing cluster 630, then processing cluster 640) may allow the transformed data streamed into the final cluster to be multiplexed such that more than one consumer may be configured to consume data from a queue of consumable data. The transform results may be routed to or pushed to different consumers or targets, for example, different long-term storage (HDFS, RDBMS, HBase, etc.) or any number of different services that satisfy a specific business use case.

Having a message cluster as the consumable cluster 650 may also enable rule-based consumers pulling data from the final repository. For example, analysis may be performed on transformed data before it arrives in the factory grid (such as notification of an admission or procedure), or transformed data may be pushed to multiple long-term storage clusters. In addition, other customers (internal or external) may be enabled to build consumers of the data that allow them to define their own business rules or long-term storage.

Moreover, traditional queuing systems may require knowing information about the consumers and where they are on the queue (the messages the consumers processed or not)—meaning the queuing system requires the information for all of the consumers it talks to. In such a traditional queuing system, if one consumer fails, eventually it will cause a failure in all consumers. Additionally, since a traditional queuing system knows what the consumers have/haven't processed, it will remove data from the queue when all consumers have processed that data. This makes reprocessing data very difficult, if not impossible (without any custom data backup implementation). Embodiments may use queuing systems that take a different approach. As described herein, the queuing cluster 630 and the consumable cluster 650 may be implemented in queuing systems that lack knowledge about the consumers. In such an embodiment, each consumer may keep its own metadata about what data it has and hasn't processed, which may be referred to as "offset in the log." Each consumer may thus consume data at its own pace. If one consumer encounters an error, it won't affect (e.g., slowing down or stalling) any other consumer. Because the exemplary queuing system does not know about the consumers processing the data, it may provide configurable data retention policies, such as, but not limited to, based on either time or storage capacity. In addition, because each consumer maintains its own "offset" of where to begin reading data from the queue, a consumer may replay all data in the queue by resetting the offset to 0 (or at least up to the time of the last data purge based on the retention policy).

Figure 7:
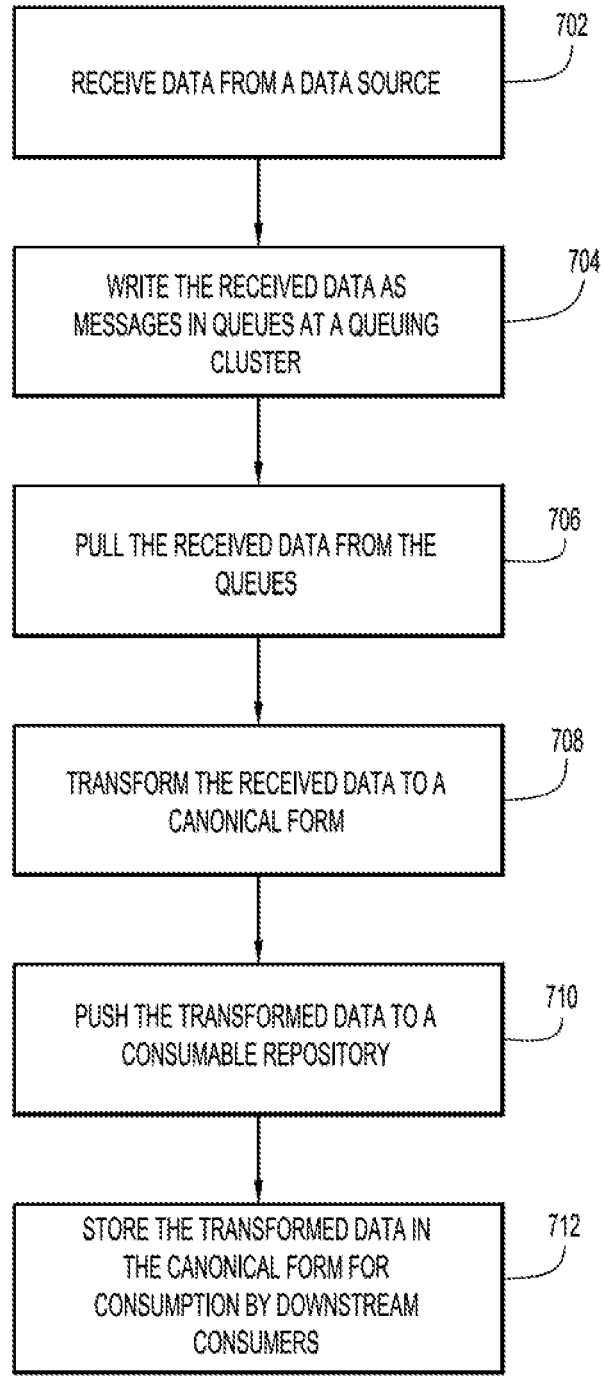
FIG. 7 is a procedural flowchart illustrating a manner of processing healthcare data from different data sources at a data center according to an embodiment of the present invention.

An exemplary method 700 in which data from various sources is queued, processed and stored for consumption according to an embodiment of the present invention is illustrated in FIG. 7. The method 700 may start at block 702, in which data may be received from a data source. In some embodiments, one or more data sources may generate data by event streams, for example, the health data gateways may obtain data from source systems produced based on occurrence of events and send the data to a data center. At block 704, the received data may be written in queues at a queuing cluster. The data center may implement a queuing cluster (e.g., the queuing cluster 630) to receive the streamed data. At block 706, the data may be pulled from the queues. For example, the processing cluster 640 may pull the data from the queuing cluster 630 for processing. At block 708, the pulled data may be transformed to a canonical form. As described herein, the processing cluster 640 may transform the data received from various gateways into canonical forms, for example, the result of the transformation is common record types. At block 710, the transformed data may be pushed to a consumable repository and at block 712, the transformed data may be stored in the canonical form for consumption by downstream consumers.

It will be appreciated that the embodiments described above and illustrated in the drawings represent only a few of the many ways of implementing embodiments for processing data from different data systems and store the processed data for various consumers.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, ingestion software, distributed processing system, queueing system, etc.). These systems may include any types of monitors and input devices (e.g., keyboard, mouse, voice recognition, etc.) to enter and/or view information.

It is to be understood that the software (e.g., ingestion software, distributed processing system, queueing system, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., ingestion software, distributed processing system, queueing system, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., messages in queues and/or consumable data, etc.). The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may utilize data in any desired structure (e.g., records, data objects, data structures, etc.), and associate the data with any desired entity (e.g., person, corporate or other business entity, healthcare or other medical related entity, healthcare provider, etc.). Present invention embodiments may be applied to any data (e.g., event streams) and may generate consumable data in any suitable form.

The present invention embodiments may employ any number of any type of user interface (e.g., Graphical User Interface (GUI), command-line, prompt, etc.) for obtaining or providing information (e.g., queries, analytic results, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for associating data from various data systems with any type of common entity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for processing streaming data, comprising:
    writing streaming data received from a data source as messages in queues at a queuing cluster, wherein the queuing duster includes a coordinator node to direct the messages to non-coordinator nodes of the queuing duster;
    retrieving the data from the queues based on subscription of topics;
    storing the retrieved data in a consumable repository;
    listening for the streaming data to be available in the queues by a processing node, the streaming data being event data for one or more events at the data source;
    reading each event from the queues by the processing node; and
    transforming the events to a data model of the consumable repository.

2. The computer-implemented method of claim 1, further comprising:
- managing the processing node by a coordinator node of a processing cluster; and
- retrying processing of the streaming data on a different processing node until successful in response to the processing node encountering a failure.

3. The computer-implemented method of claim 1, wherein the streaming data includes patient data received from a healthcare network.

4. The computer-implemented method of claim 1, wherein the consumable repository is a queuing system including a coordinator node to direct the processing node to write the retrieved data to a non-coordinator node in the consumable repository.

5. The computer-implemented method of claim 4, wherein the queuing cluster and consumable repository each include multiple non-coordinator nodes that provide automated replication and failover through management by the respective coordinator nodes.

6. The computer-implemented method of claim 1, further comprising one or more from a group of:
- routing the retrieved data to different long term storage; and
- pushing the retrieved data to a number of different services that satisfy specific business needs.

7. The computer-implemented method of claim 1, further comprising:
- concurrently retrieving data from the consumable repository by a plurality of consumers, wherein the consumers maintain respective pointers to track data that each consumer has processed.

* * * * *